United States Patent
Davis et al.

[11] Patent Number: 6,048,326
[45] Date of Patent: Apr. 11, 2000

[54] DISPOSABLE ELASTIC THERMAL KNEE WRAP

[75] Inventors: Leane Kristine Davis, Milford; Ronald Dean Cramer; William Robert Ouellette, both of Cincinnati; Dawn Michele Kimble, Sharonville, all of Ohio

[73] Assignee: The Procter & Gamble Company, Cincinnati, Ohio

[21] Appl. No.: 08/984,366

[22] Filed: Dec. 3, 1997

Related U.S. Application Data

[63] Continuation-in-part of application No. 08/775,210, Dec. 31, 1996, Pat. No. 5,860,945.

[51] Int. Cl.⁷ .................. A61F 13/00; A61F 7/00
[52] U.S. Cl. .................. 602/26; 602/62; 607/108
[58] Field of Search .................. 602/2, 60–63, 602/75, 26; 607/108–114

[56] References Cited

U.S. PATENT DOCUMENTS

| | | | |
|---|---|---|---|
| Re. 32,026 | 11/1985 | Yamashita et al. | 126/263 |
| 1,491,539 | 4/1924 | Kirschmann | 607/109 |
| 1,727,897 | 9/1929 | Myers et al. | 602/62 |
| 2,547,886 | 4/1951 | Poux | 62/1 |
| 2,562,121 | 7/1951 | Poux | 150/2.2 |
| 2,602,302 | 7/1952 | Poux | 62/1 |
| 3,463,161 | 8/1969 | Andrassy | 128/402 |
| 3,900,035 | 8/1975 | Welch et al. | 128/402 |
| 3,945,046 | 3/1976 | Stromgren | 2/22 |
| 4,095,583 | 6/1978 | Petersen et al. | 126/263 |
| 4,205,685 | 6/1980 | Yoshida et al. | 128/399 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,470,417 | 9/1984 | Gruber | 128/402 |
| 4,516,564 | 5/1985 | Koiso et al. | 126/263 |
| 4,573,447 | 3/1986 | Thrash et al. | 607/111 |
| 4,575,097 | 3/1986 | Brannigan et al. | 128/402 |
| 4,586,506 | 5/1986 | Nangle | 128/403 |
| 4,628,932 | 12/1986 | Tampa | 128/402 |
| 4,649,895 | 3/1987 | Yasuki et al. | 126/263 |
| 4,671,267 | 6/1987 | Stout | 128/156 |
| 4,688,572 | 8/1987 | Hubbard et al. | 128/402 |
| 4,748,975 | 6/1988 | Yashima | 602/60 |
| 4,753,241 | 6/1988 | Brannigan et al. | 128/380 |
| 4,756,299 | 7/1988 | Podella | 126/263 |
| 4,805,620 | 2/1989 | Meistrell | 128/402 |

(List continued on next page.)

FOREIGN PATENT DOCUMENTS

| | | | |
|---|---|---|---|
| 0 370 600 A1 | 7/1989 | European Pat. Off. | F24J 1/00 |
| 160443 | 9/1983 | India | C09K 3/02 |
| 56-145846 | 11/1981 | Japan | A61F 7/03 |
| 57-170252 | 10/1982 | Japan | A61F 7/03 |
| 58-37075 | 3/1983 | Japan | C09K 5/00 |
| 3-100090 | 4/1991 | Japan | C09K 5/00 |
| 5-317188 | 12/1993 | Japan | A47J 36/28 |

(List continued on next page.)

*Primary Examiner*—Richard J. Apley
*Assistant Examiner*—Denise Pothier
*Attorney, Agent, or Firm*—Loy M. White; Douglas C. Mohl; T. David Reed

[57] ABSTRACT

The present invention relates to disposable elastic thermal knee wraps having one or more thermal packs comprising a plurality of heat cells, wherein heat is applied to the user's knee. More particularly, the present invention relates to disposable elastic thermal knee wraps having good conformity to user's knee which provide consistent, convenient and comfortable heat application.

30 Claims, 2 Drawing Sheets

U.S. PATENT DOCUMENTS

| | | | |
|---|---|---|---|
| 4,860,748 | 8/1989 | Chiurco et al. | 128/399 |
| 4,886,063 | 12/1989 | Crews | 128/403 |
| 4,925,743 | 5/1990 | Ikeda et al. | 428/702 |
| 5,000,176 | 3/1991 | Daniel | 128/402 |
| 5,025,777 | 6/1991 | Hardwick | 126/263 |
| 5,027,801 | 7/1991 | Grim | 128/80 H |
| 5,046,479 | 9/1991 | Usui | 126/204 |
| 5,072,598 | 12/1991 | Dibrell | 62/259.3 |
| 5,086,761 | 2/1992 | Ingram | 602/26 |
| 5,125,392 | 6/1992 | Hardwick | 126/263 |
| 5,139,476 | 8/1992 | Peters | 602/26 |
| 5,139,477 | 8/1992 | Peters | 602/26 |
| 5,148,804 | 9/1992 | Hill et al. | 128/402 |
| 5,179,944 | 1/1993 | McSymytz | 128/403 |
| 5,190,033 | 3/1993 | Johnson | 128/403 |
| 5,211,949 | 5/1993 | Salyer | 602/2 |
| 5,233,981 | 8/1993 | Miyashita | 607/114 |
| 5,342,412 | 8/1994 | Ueki | 607/114 |
| 5,366,492 | 11/1994 | Ueki | 607/114 |
| 5,395,399 | 3/1995 | Rosenwald | 107/108 |
| 5,399,153 | 3/1995 | Caprio, Jr. et al. | 602/62 |
| 5,405,671 | 4/1995 | Kamin et al. | 428/69 |
| 5,409,500 | 4/1995 | Dyrek | 607/111 |
| 5,415,624 | 5/1995 | Williams | 602/2 |
| 5,451,201 | 9/1995 | Prengler | 602/26 |
| 5,462,519 | 10/1995 | Carver | 602/47 |
| 5,496,357 | 3/1996 | Jensen et al. | 607/108 |
| 5,496,358 | 3/1996 | Rosenwald | 607/108 |
| 5,603,727 | 2/1997 | Clark et al. | 607/108 |
| 5,674,270 | 10/1997 | Viltro et al. | 607/112 |
| 5,741,318 | 4/1998 | Ouellette et al. | 607/108 |
| 5,925,072 | 7/1999 | Cramer et al. | 607/108 |

FOREIGN PATENT DOCUMENTS

| | | | |
|---|---|---|---|
| 6-1969 | 1/1994 | Japan | C09K 5/00 |
| 6-315498 | 11/1994 | Japan | A61F 7/08 |
| 6-343658 | 12/1994 | Japan | A61F 7/08 |
| 7-67907 | 3/1995 | Japan | A61F 7/08 |
| 7-124192 | 5/1995 | Japan | A61F 7/08 |
| 7-49042 | 5/1995 | Japan | A61F 7/08 |
| 7-194641 | 8/1995 | Japan | A61F 7/08 |
| 7-194642 | 8/1995 | Japan | A61F 7/08 |
| 8-98856 | 4/1996 | Japan | A61F 7/08 |
| 8-126656 | 5/1996 | Japan | A61F 7/08 |
| 2 205 496 | 12/1988 | United Kingdom | A61F 7/03 |
| WO 94/00087 | 1/1994 | WIPO | A61F 7/00 |

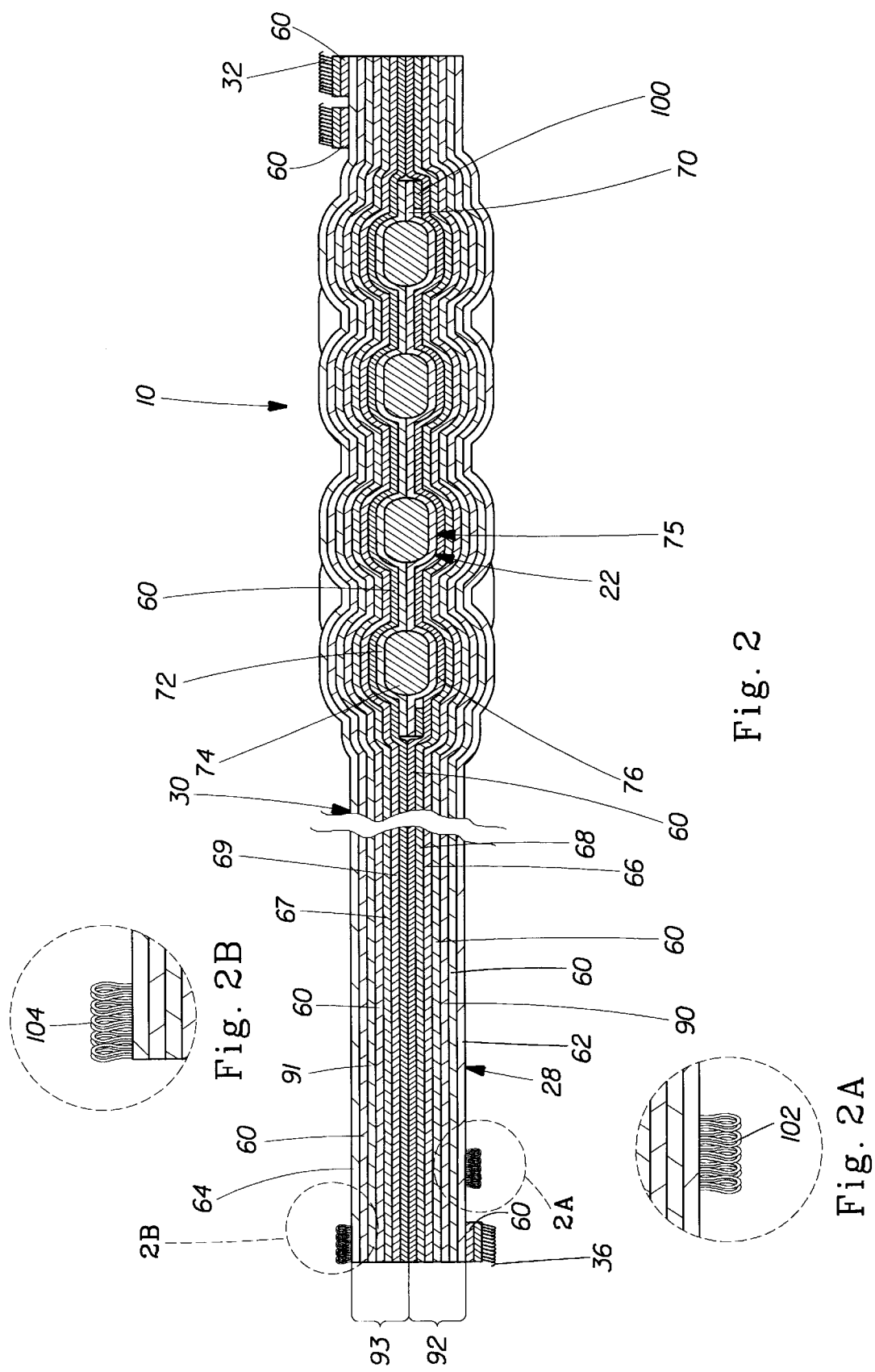

DISPOSABLE ELASTIC THERMAL KNEE WRAP

CROSS REFERENCE TO RELATED APPLICATION

This application is a continuation-in-part of application Ser. No. 08/775,210, filed Dec. 31, 1996, now U.S. Pat. No. 5,860,945.

TECHNICAL FIELD

The present invention relates to disposable elastic thermal knee wraps having one or more thermal packs comprising a plurality of individual heat cells, wherein heat is applied to specific areas of the user's knee. More particularly, the present invention relates to disposable elastic thermal knee wraps having good conformity to user's knee which provide consistent, convenient and comfortable heat application.

BACKGROUND OF THE INVENTION

A common method of treating temporary or chronic pain is by application of heat to the afflicted area. Such heat treatments are used as a means of therapy for conditions which include aches, stiffness in muscles and joints, nerve pain, rheumatism and the like. Typically, the method for relieving pain using heat treatments has been to topically apply a relatively high heat, i.e., greater than about 40° C., for a short period of time, i.e., from about twenty minutes to about one hour.

The human knee is one of the most vulnerable joints of the human body to overstress injury. While elastic compression bandages have been used to help stabilize knee movement during injury healing, heating pads, whirlpools, hot towels, hot water bottles, hot packs, and hydrocollators have been commonly used to apply heat to the knee to relieve the pain of knee injury. These pain relieving and stabilization devices, however, typically provide either one function or the other, but not both. Further, many of these devices are inconvenient to use on a regular and extended basis because the heat energy may not be immediately available when needed or released in a controllable manner. That is, many of these thermal units or devices do not provide long lasting heat and also do not maintain a consistent temperature over long periods of time. Proper positioning of the thermal energy also may not be maintainable during knee flexure. In general, the beneficial therapeutic effects from this administration of heat diminish after the heat source is removed.

The present inventors, however, have discovered that maintaining a sustained skin temperature of from about 32° C. to about 50° C., preferably from about 32° C. to about 45° C., more preferably from about 32° C. to about 42° C., most preferably from about 32° C. to about 39° C., still most preferably from about 32° C. to about 37° C. for a period of from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment, such that the desired therapeutic benefits are achieved without any adverse events, such as skin burns which may be incurred by using a high temperature for a long period of time, substantially relieves acute, recurrent, and/or chronic knee pain, including skeletal, muscular, and/or referred knee pain, of a person having such pain.

The present inventors have further discovered that preferably maintaining a sustained skin temperature of from about 32° C. to about 43° C., preferably from about 32° C. to about 42° C., more preferably from about 32° C. to about 41° C., most preferably from about 32° C. to about 39° C., still most preferably from about 32° C. to about 37° C., for a time period of greater than about 1 hour, preferably greater than about 4 hours, more preferably greater than about 8 hours, even more preferably greater than about 16 hours, most preferably about 24 hours, substantially relieves acute, recurrent, and/or chronic knee pain, including skeletal, muscular, and/or referred knee pain, of a person having such pain and substantially prolongs relief even after the heat source is removed from the user's knee.

Disposable heat packs based on iron oxidation, such as those described in U.S. Pat. Nos. 4,366,804, 4,649,895, 5,046,479 and Re. 32,026, are known. However, such devices have proven not totally satisfactory because many of these devices are bulky, cannot maintain a consistent and controlled temperature, have difficulty staying in place during use, and/or have unsatisfactory physical dimensions which hinder their effectiveness. Specifically, such devices cannot be easily incorporated into wraps which comfortably and reliably conform to various body contours, and hence, deliver inconsistent, inconvenient and/or uncomfortable heat application to the body.

The present inventors have developed disposable elastic thermal knee wraps which provide both compression and thermal energy in a controlled and sustainable manner. These wraps comprise one or more thermal packs having a unified structure, wherein each thermal pack has at least one continuous layer, preferably of a semirigid material, which is sufficiently rigid in specific areas of the thermal pack, yet which softens in between such areas when heated during use, most preferably comprising a coextruded film of polypropylene and ethylene vinyl acetate (EVA). The thermal pack or packs also comprise a plurality of individual heat cells, which typically comprise an exothermic composition, preferably comprising a specific iron oxidation chemistry, and having specific physical dimensions and fill characteristics, spaced apart and fixed within or to the unified structure of the thermal pack. Active heat cells, that is, heat cells having a temperature of about 35° C. or greater, preferably soften narrow portions of the continuous layer or layers of semirigid material which immediately surround the heat cells. Any remaining portions of the continuous layer or layers which surround the softened portions preferably remain more rigid. The narrow, softened portions act as hinges between the heat cells and between any remaining, cooler, more rigid portions, bending preferentially more than either the heat cells or more rigid portions. This results in thermal packs which possess sufficient rigidity to maintain structural support of the heat cells, to prevent unacceptable stretching of structures of the continuous layer or layers during processing or use, and to deter easy access to heat cell contents, while still maintaining good overall drape characteristics when heated. The thermal pack or packs, when incorporated into the knee wraps of the present invention, provide efficient and effective heat coverage by having excellent conformity with the user's knee. These wraps also comprise alignment and bunching resistance features.

The present inventors have also discovered that it may be desirable to selectively place heat cells, in the thermal pack or packs when incorporated into the knee wraps of the present invention, into positions fixed within or to the unified structure of the thermal pack, relative to each other which are sufficiently close so as to block some or all possible axes, which otherwise would have passed uninterrupted between the heat cells, through the thermal pack, or select regions thereof, to minimize or eliminate undesirable, uninterrupted fold lines, and/or to increase the structural support that the heat cell matrix imparts to the thermal pack. That is, placement of the heat cells into positions relative to each other which are sufficiently close to block some or all possible axes which would otherwise have passed uninterrupted, between the heat cells, causes the thermal packs to fold along a multiplicity of short interconnected fold lines oriented in a number of different directions relative to each other. Folding along a multiplicity of interconnected fold lines results in good overall drape characteristics.

It is therefore an object of the present invention to provide disposable elastic knee wraps which comprise one or more thermal packs, comprising a unified structure of at least one continuous layer, preferably of a semirigid material which has different stiffness characteristics over a range of temperatures, and a plurality of individual heat cells, which provide a controlled and sustained temperature and which reach their operating temperature range relatively quickly. The heat cells are spaced apart and fixed within or to the unified structure of the thermal pack.

It is also an object of the present invention to provide disposable thermal knee wraps having good overall drapability while maintaining sufficient rigidity to maintain structural support of the heat cells and to prevent unacceptable stretching of the continuous layer or layers during processing or use.

It is a further object of the present invention to provide disposable elastic thermal knee wraps which provide consistent, convenient and comfortable heat application while deterring easy access to heat cell contents.

It is a still further object of the present invention to provide methods of treating acute, recurrent, and/or chronic knee pain, including skeletal, muscular, and/or referred knee pain, of a person suffering from such pain, by maintaining a sustained skin temperature of from about 32° C. to about 50° C. for a period of time of from about twenty seconds to about twenty-four hours, preferably by maintaining a skin temperature of from about 32° C. to about 43° C. for a time period of greater than about 1 hour to provide prolonged relief from such pain.

These objectives and additional objectives will become readily apparent from the detailed description which follows.

SUMMARY OF THE INVENTION

The disposable elastic thermal knee wraps of the present invention, comprise at least one piece of flexible material having an outer surface, a body-facing surface, a first end, a second end, and an elastic portion stretchable along a longitudinal axis of the piece of flexible material. The piece of flexible material has a length great enough to encircle a user's knee such that the first and second ends overlap. The first and second ends comprise a reclosable fastening system, preferably a hook and loop fastening system, for attaching the first end to the second end in order to hold the disposable elastic thermal knee wrap around the user's knee. The piece of flexible material also comprises an aperture therein intended to be aligned with the user's patella to establish a convenient locating point for wrapping the knee wrap around the user's knee. The piece of flexible material further comprises a slit extending substantially along the longitudinal axis from the aperture for enabling the piece of flexible material to stretch transverse to the longitudinal axis at the aperture in order to accommodate bending of the user's knee.

The disposable elastic thermal knee wraps of the present invention further comprise one or more thermal packs. The thermal pack or packs comprise a unified structure having at least one continuous layer of material, which is preferably semirigid at a temperature of about 25° C., having a tensile strength of about 0.7 g/mm² or greater, and at least two-dimensional drape, and which is substantially less rigid at a temperature of 35° C. or greater, having a tensile strength substantially less than the tensile strength of the material at about 25° C.

The continuous layer or layers of the present invention preferably comprise a coextruded material, more preferably a coextruded material comprising polypropylene, most preferably a coextruded material wherein a first side comprises polypropylene and a second side comprises a tie-layer of a low melt temperature copolymer, preferably EVA, preferably having a combined basis weight thickness of less than about 50 μm.

The thermal pack or packs further comprise a plurality of individual heat cells, which preferably comprise a mixture of powdered iron, powdered carbon, water, and salt, which when exposed to oxygen, provide a controlled and sustained temperature and which reach their operating temperature range quickly. The heat cells are spaced apart and fixed within or to the unified structure of the thermal pack. Preferably the heat cells are placed into positions fixed within or to the unified structure of the thermal pack, relative to each other and sufficiently close so that some or all of the possible axes that would otherwise pass uninterrupted between the heat cells are blocked by the heat cells to cause the thermal packs to fold along a multiplicity of short interconnected fold lines.

The disposable elastic thermal knee wraps of the present invention preferably comprise a plurality of glue stays bonded transverse to the longitudinal axis of the piece of flexible material to resiliently stiffen the flexible material and thereby minimize bunching of the flexible material when the user's knee is repeatedly bent.

The disposable elastic thermal knee wraps of the present invention also preferably comprise a fastening means having a plurality of hook members which engage loop fibers of a landing zone attached to the piece of flexible material in order to adjust the wrap to a user's knee and to attain a comfortable level of elastic tension.

The present invention still further comprises methods of treating acute, recurrent, and/or chronic knee pain, including skeletal, muscular, and/or referred knee pain, of a person having such pain, by applying the disposable elastic thermal knee wraps of the present invention to the knee of a person having such pain, to maintain a sustained skin temperature of from about 32° C. to about 50° C. for a period of time of from about twenty seconds to about twenty-four hours, preferably to maintain a skin temperature of from about 32° C. to about 43° C. for a time period of greater than about 1 hour, to provide prolonged relief from such pain.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 2 is a sectioned side elevation view of FIG. 1, disclosing the laminate structure of the wrap.

DETAILED DESCRIPTION OF THE INVENTION

Figure 1:
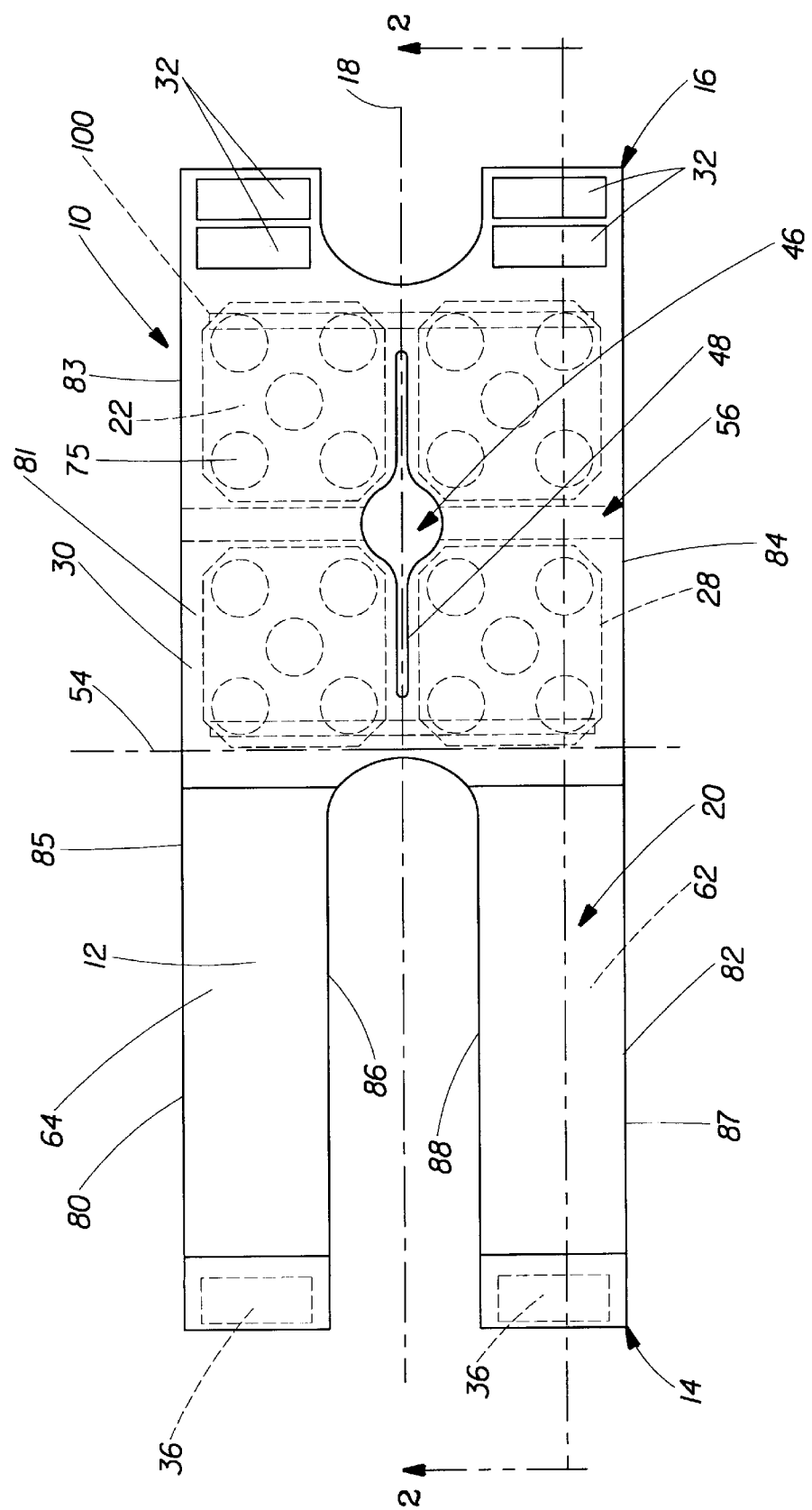
FIG. 1 is a top plan view of a preferred embodiment of the disposable elastic thermal knee wrap of the present invention, showing a preferred pattern of thermal pack(s) and/or heat cells embedded therein.

The disposable elastic thermal knee wraps of the present invention comprise one or more thermal packs having at least one continuous layer of a material which preferably exhibits specific thermophysical properties, and a plurality of individual heat cells which preferably comprise an exothermic composition, spaced apart and fixed within or to the structure of the disposable thermal pack.

The material of the at least one continuous layer is preferably semirigid when at room temperature, i.e., about 25° C., or below, but softens and becomes substantially less rigid when heated to about 35° C., or greater. Therefore, when heat cells, which are fixed within or to the unified structure of the thermal packs, are active, that is at a heat cell temperature of about 35° C. or greater, the narrow portion of the continuous layer or layers of material immediately surrounding each heat cell preferably softens and acts as a hinge between the heat cells and between any remaining more rigid portion of the continuous layer or layers, bending preferentially more than either the heat cells or any cooler, more rigid portions. This results in a thermal packs which possess sufficient rigidity to maintain structural support of the heat cells and prevent unacceptable stretching of structures of the continuous layer or layers during processing or use, while still maintaining good overall drape characteristics when heated. The disposable elastic thermal knee wraps of the present invention, provide consistent, convenient, and comfortable heat application, and an excellent conformity to the user's knee, while retaining sufficient rigidity to deter easy access to heat cell contents.

"Disposable", as used herein, means that, while the thermal knee wraps of the present invention may be stored in a resealable, substantially air-impermeable container and reapplied to the user's body as often as required for the relief of pain, they are intended to be thrown away, i.e., deposited in a suitable trash receptacle, after the heat source, i.e., the heat cell(s) or thermal pack(s), has been fully expended.

"Heat cells", as used herein, means a unified structure, comprising an exothermic composition, preferably a specific iron oxidation chemistry, enclosed within two layers, wherein at least one layer may be oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps, pads, and the like. Thermal packs and body wraps incorporating thermal packs adapt to a wide variety of body contours, thus providing consistent, convenient, and comfortable heat application.

"Plurality of heat cells", as used herein, means more than one, preferably more than two, more preferably more than three, most preferably more than four, heat cells.

"Agglomerated pre-compaction composition", as used herein, means the mixture of dry powdered ingredients, comprising iron powder, carbonaceous powder, metal salt (s), water-holding agent(s), agglomeration aid(s), and dry binder(s) prior to direct compaction.

"Direct compaction", as used herein, means a dry powder mixture is blended, compressed, and formed into pellets, tablets, or slugs without the use of typical wet binders/ solutions to adhere the particulate(s) together. Alternatively, the dry powder mixture is blended and roll compacted or slugged, followed by milling and screening, creating directly compacted granules. Direct compaction may also be known as dry compaction.

"Heating element(s)", as used herein, means the exothermic, direct compacted, dry agglomerated pre-compaction composition formed into compaction articles, such as granules, pellets, slugs, and/or tablets capable of generating heat, after an aqueous solution such as water or brine (salt solution) is added, by the exothermic oxidation reaction of iron. Agglomeration granules of said agglomerated pre-compaction composition are also included as heating elements herein.

The "fill volume", as used herein, means the volume of the particulate composition or the compacted, water-swelled, heating element in the filled heat cell. The "void volume", as used herein, means the volume of the cell left unfilled by the particulate composition or the compacted, water-swelled, heating element in a finished heat cell, not including the unfilled space within a tablet comprising a hole or reservoir, in a finished heat cell, measured without differential pressure in the heat cell and without additional stretching or deformation of the substrate material. The "cell volume", as used herein, means the fill volume plus the void volume of the heat cell.

"Continuous layer or layers", as used herein, means one or more layers of a material which may be uninterrupted or partially, but not completely, interrupted by another material, holes, perforations, and the like, across its length and/or width.

"Rigid", as used herein, means the property of a material wherein the material may be flexible, yet is substantially stiff and unyielding, and which does not form fold lines in response to gravitational pull or other modest forces.

"Semirigid material", as used herein, means a material which is rigid to some degree or in some parts, i.e., having at least two-dimensional drape at a temperature of about 25° C., and exhibits a toughness to maintain structural support of the heat cells in an unsupported format, and/or to prevent unacceptable stretching of structures of the material during processing or use, while still maintaining good overall drape characteristics when heated, and/or retaining sufficient rigidity to deter easy access to deter easy access to heat cell contents.

"Two dimensional drape", as used herein, means drape which occurs across a continuous layer or layers, across a thermal pack, or across a select region of a layer or layers, or thermal pack, exclusively along one axis, i.e., one fold line forms, at the expense of other fold lines in response to gravitational pull or other modest forces.

"Three dimensional drape", as used herein, means drape which simultaneously occurs across a continuous layer or layers, across a thermal pack, or across a select region of a layer or layers, or thermal pack, along two or more axes, i.e., two or more fold lines form, in response to gravitational pull or other modest forces.

"Fold lines", as used herein, means the line along which a material forms a temporary or permanent crease, ridge, or crest in response to gravitational pull or other modest forces.

It is understood that the disposable elastic thermal knee wraps of the present invention may contain one or more thermal packs. However, for clarity, a disposable elastic thermal knee wrap comprising a single thermal pack will be described herein.

Referring now to the drawings, and more particularly to FIGS. 1 and 2, there is shown a preferred embodiment of the present invention, which provides a disposable elastic thermal knee wrap, generally indicated as 10. Elastic thermal knee wrap 10 comprises at least one substantially rectangular piece of flexible material 12 having a longitudinal axis 18. Flexible material 12 has a first end 14 and a second end 16 and an elastic portion 20 therebetween capable of being stretched along longitudinal axis 18. Flexible material 12 has a length, as measured in a direction parallel to longitudinal axis 18 from first end 14 to second end 16, when in a relaxed or stretched state, which is great enough to encircle a user's knee, such that first end 14 overlaps second end 16 when wrap 10 is positioned around user's knee. Flexible material 12 of knee wrap 10 has a body-facing surface 28 and an outer surface 30 extending from first end 14 to second end 16.

As used herein, "elastic" refers to that property of a material whereby the material, when subjected to a tensile force, will stretch or expand in the direction of the force and will essentially return to its original untensioned dimension upon removal of the force. More specifically, the term "elastic" is intended to mean a directional property wherein an element or structure has a recovery to within about 10% of its original length $L_o$ after being subjected to a percent strain $\epsilon_\%$ of greater than 50%. As used herein, percent strain $\epsilon_\%$ is defined as:

$$\epsilon_\% = [(L_f - L_o)/L_o] * 100$$

Where
$L_f$ = Elongated Length
$L_o$ = Original Length

For consistency and comparison, the recovery of an element or structure is preferably measured 30 seconds after release from its elongated length $L_f$. All other elements or structures will be considered inelastic if the element or structure does not recover to within about 10% of its original length $L_o$ within 30 seconds after being released from a percent strain $\epsilon_\%$ of 50%. Inelastic elements or structures would also include elements or structures which fracture and/or permanently/plastically deform when subjected to a percent strain $\epsilon_\%$ of 50%.

Flexible material 12 of wrap 10 further comprises a first elastic member 66. First elastic member 66 is preferably thermally bonded to first carrier layer 68 prior to assembly of flexible material 12 of wrap 10 to form a first thermal bonded laminate. First elastic member 66, thermal bonded to first carrier layer 68 is then fixedly attached to first bulking layer 90 and body-facing material 62 by hot melt adhesive layers 60 to form body-facing laminate 92.

Similarly, flexible material 12 of wrap 10 further comprises a second elastic member 67. Second elastic member 67 is preferably thermally bonded to second carrier layer 69 prior to assembly of flexible material 12 of wrap 10 to form a second thermal bonded laminate. Second elastic member 67, thermal bonded to second carrier layer 69 is then fixedly attached to second bulking layer 91 and outer surface material 64 by hot melt adhesive layer 60 to form outer surface laminate 93. Body-facing laminate 92 is then fixedly attached to outer surface laminate 93 with one or more thermal packs 22 interposed therebetween to form wrap 10.

In a particularly preferred embodiment of the present invention, first elastic layer 66 is integrally thermally bonded on a first side to first carrier layer 68 and on a second side to second carrier layer 69, i.e., double thermal bonded scrim.

To improve the elastic performance of wrap 10, elastic portion 20 may be subjected to an activation process after assembly and prior to use. This activation process stretches and permanently deforms on a very small scale the nonelastic layers of wrap 10 within elastic portion 20. This activation process allows the first elastic member 66 and second elastic member 67 of elastic portion 20 to stretch or expand in the direction of an applied force and essentially return to their original dimensions upon removal of the force, unencumbered by the nonelastic layers of elastic portion 20.

Alternatively, elastic portion 20 of wrap 10 may be assembled while elastic member or members 66 and/or 67 are held in an extended state. After assembly, the elastic member or members 66 and/or 67 are allowed to return to their relaxed state causing the nonelastic layers of elastic portion 20 to fold and buckle creating rugosities. Subsequent stretching of elastic portion 20 will result in the unfolding of these rugosities.

In a preferred embodiment of the present invention there is a second elastic portion 56 located intermediate thermal packs 22. Materials and processes used to deliver elastic portion 20 may also be used to deliver second elastic portion 56.

A particular embodiment of wrap 10 has been described which has two elastic members which are coextensive body-facing material 62 and outer surface material 64. Preferably, the elastic member or members 66 and/or 67 extend from first end 14 to interfacial centerline 54 of flexible material 12 to provide elastic properties to elastic portion 20. Interfacial centerline 54 is preferably aligned perpendicular to longitudinal axis 18 located between first end 14 and second end 16. Additional elastic members may also be located intermediate thermal packs 22 to provide elastic properties to second elastic portion 56.

Body-facing material 62 and outer surface material 64 may be any number of different materials which include, but are not limited to, woven and knit fabrics, carded nonwovens, spunbond nonwovens, and the like. A material that has been found to be particularly suitable for body-facing material 62 and outer surface material 64 is a carded thermally bonded nonwoven of polypropylene with a basis weight of 32 g/m$^2$ (27 grams per square yard (gsy)). This material is available as grade #9327786, from Veratec, Walpole, Mass.

First elastic member 66 and second elastic member 67 may each be selected from natural or synthetic rubber, or any number of polymeric materials which are capable of elongation and recovery. Suitable materials include, but are not limited to, styrene block copolymers, rubber, Lycra™, Krayton™, polyethylene including metallocene catalyst PE, foams including polyurethane and polyesters, and the like. First elastic member 66 and second elastic member 67 may be in the form of films, strands, scrims, ribbons, tapes, structural elastic-like film, and the like. A particularly suitable material for use as first elastic member 66 and second elastic member 67 is an elastic scrim available as T50018 from Conwed Plastics, Minneapolis, Minn.

First carrier layer 68 and second carrier layer 69 may be any number of different material which include, but are not limited to, woven or knit fabrics, carded nonwovens, spunbond nonwovens, and the like. A material that has been found to be particularly suitable for first carrier layer 68 and second carrier layer 69 is a carded thermally bonded non-woven of polypropylene with a basis weight of 32 g/m$^2$ (27 gsy). This material is available as grade #9327786 from Veratec, Walpole, Mass.

First bulking layer 90 and second bulking layer 91 may be any number of different materials which include, but are not limited to, woven and knit fabrics, formed films, carded nonwovens, spunbond nonwovens, and the like. A material that has been found to be particularly suitable for first bulking layer 90 and second bulking layer 91 is a polyethylene formed film available as C3265 from Tredegar Film Products, Terre Haute, Ind.

The attachment of layers to form body-facing laminate 92, outer surface laminate 93 and, finally, wrap 10 may be achieved by any number of attachment means known in the art. These include, but are not limited to, hot melt adhesive including spiral sprays, meltblown, control coat, and the like, latex adhesives applied via spray, printing gravure, and the like, thermal bonding, ultrasonic, pressure bonding, and the like. One particular method that has been used successfully is hot melt adhesive layers 60 available as 70-4589 from National Starch and Chemical Co., Bridgewater, N.J., applied via a spiral hot melt system at a rate of about 0.77 to 1.55 mg/cm$^2$ (5 to 10 mg per square inch).

A particular embodiment of wrap 10 has been described which utilizies a number of layers. Alternatively, wrap 10 could be comprised of a single elastic member. First carrier layer 68 and second carrier layer 69 are employed during the thermal bonding of first elastic member 66 and second elastic member 67. If the thermal bonding step is not used for any number of reasons then first carrier layer 68 and second carrier layer 69 may be omitted. Similarly, first bulking layer 90 and second bulking layer 91 are used to deliver a perceptibly thicker product. These layers may also be omitted and still remain within the scope of the present invention.

Body-facing surface 28 of flexible material 12 comprises body-facing material 62 coextensive from first end 14 to second end 16. Body-facing material 62 comprises a plurality of loop elements 102 which are formed from fibers of material 62. Similarly, outer surface 30 of flexible material 12 comprises outer surface material 64 coextensive from first end 14 to second end 16. Outer facing material 64 comprises a plurality of loop elements 104 which are formed from fibers of material 64. The plurality of loop elements 102 and 104 serve as one-half of a reclosable two-part hook and loop fastening system. As used herein the term reclosable refers to that property of a fastening system which provides for initial closing of the fastening system, a subsequent opening of the fastening system, followed by at least one additional closings of the same fastening system. The subsequent closing of the fastening system may either return the closure to the original position or it may result in a repositioning of the closure from the initial configuration.

Body-facing surface 28 of flexible material 12 comprises a plurality of hook members 36 which are permanently attached to body-facing surface 28 near first end 14. Similarly, outer surface 30 of flexible material 12 comprises a plurality of hook members 32 which are permanently attached to outer surface 30 near second end 16. The plurality of hooks on hook members 32 and 36 serve as the second half of a reclosable two-part hook and loop fastening system. As used herein, the term permanently attached is defined as the joining of two or more elements which remain joined during their intended use.

Hook members 32 with loop elements 102 and hook members 36 with loop elements 104, provide a reclosable hook and loop fastening system for securing wrap 10 around the user's knee.

The hooks of hook members 32 and 36 may be any number of styles, shapes, and/or densities depending upon the use. The hooks of hook members 32 and 36 may be bent shafts, mushroom capped, harpoon-shaped, or any other suitable shape. The hooks of hook members 32 and 36 may be unidirectional, bi-directional, or omni-directional depending upon the application and companion loop elements of loop members 102 and 104. The hooks of hook members 32 and 36 must be chosen in conjunction with companion loop elements of loop members 102 and 104 so as to provide the peel and shear forces that are required for different applications.

Alternatively, the reclosable fastening system of wrap 10 may be a single hook and loop fastening system comprising either hook members 32 and loop elements 102 or hook members 36 and loop elements 104.

Flexible material 12 further comprises an upper strap portion 80 and a lower strap portion 82, each having at least one hook member 36 which can be independently fastened to loop members 104. Upon application of wrap 10, first end 14 of upper strap portion 80 encircles behind the user's leg above the knee and first end 14 of lower strap portion 82 encircles behind the user's leg below the knee. First end 14 of upper strap portion 80 and first end 14 of lower strap portion 82 overlap second end 16 such that, hook members 32 on outer surface 30 near second end 16 engage loop elements 102 on body-facing surface 28. Engagement of hook members 32 with loop elements 102 forms the first part of a two part hook and loop fastening system. Continuing the application, hook members 36 on the body-facing surface 28 near first end 14 are placed in contact with loop elements 104 of outer surface 30 forming the second part of a two part hook and loop fastening system. Upper strap portion 80 and lower strap portion 82 allow easier application and differential tensioning of material 12 during use.

Preferably, upper strap portion 80 and lower strap portion 82 contain elastic portion 20 of flexible material 12. That is upper strap portion 80 and lower strap portion 82 preferably exhibit elastic behaviour when stretched in a direction parallel to longitudinal axis 18.

Flexible web 12 further comprises a body portion 81. Body portion 81 of flexible material 12 has a first edge 83 and a second edge 84. The distance between first edge 83 and second edge 84 measured in a direction transverse longitudinal axis 18 is the width of body portion 81 of flexible material 12. Upper strap portion 80 of flexible material 12 has a first edge 85 and a second edge 86. The distance between first edge 85 and second edge 86 measured in a direction transverse longitudinal axis 18 is the width of upper strap portion 80 of flexible material 12. Lower strap portion 82 of flexible material 12 has a first edge 87 and a second edge 88. The distance between first edge 87 and second edge 88 measured in a direction transverse longitudinal axis 18 is the width of lower strap portion 82 of flexible material 12.

Preferably, the width of body portion 81 of flexible material 12 is from about 15 cm to about 25 cm, more preferably from about 18 cm to about 23 cm and most preferably from about 19 cm to about 21 cm. The width of upper strap portion 80 and lower strap portion 82 of flexible material 12 is typically less than the width of body portion 81 of flexible material 12, and preferably from about 2.5 cm to about 13 cm, more preferably from about 4 cm to about 8 cm, and most preferably form about 5 cm to about 7 cm.

Flexible material 12 further has an aperture 46 between interfacial centerline 54 and second end 16. Aperture 46 is intended to be aligned with the wearer's patella and serves to help properly position wrap 10 during use. Extending from aperture 46, material 12 has at least one slit 48, preferably two slits, extending from aperture 46, one toward second end 16 and the other toward interfacial centerline 54.

Slit(s) 48 allows material 12 to expand and close respectively as the user bends and straightens the knee. Slit(s) 48 may be of any shape, however, the rectangular shape, as depicted in FIG. 1, is preferred. It is also preferred, for the embodiment as depicted in FIG. 1, that slit(s) 48 be from about 15 cm to about 18 cm (about 6 to about 7 inches) in length.

Stays 100 are preferably embedded transverse to the longitudinal axis 18 and internally in the layers of flexible material 12 of wrap 10 and positioned adjacent interfacial centerline 54 and/or second end 16 of material 12. Stays 100 are preferably stripes of glue which are positioned to permit the wrap 10 to bend with the knee, but minimizes bunching of the flexible material 12, which would otherwise occur after several knee bending cycles. Stays 100 serve as resilient stiffeners to cause the wrap 10 to maintain its flatness against the user's leg. Alternatively, the stays 100 may be positioned on the outer surface 30 of wrap 10. Typically, the stays 100 extend to just short of the perimeter edges of wrap 10 so that the stiff ends of glue stays 100 are never in contact with wrap 10 user's leg. However in a second alternative, the stays 100 may be positioned on the body-facing surface 28 of wrap 10 to increase friction between the knee wrap and user's leg in order to reduce slippage of wrap 10 during use.

The preferred glue for stays 100 is HL1460-X made by Fuller, Minneapolis, Minn. Beads of about 5 mm in diameter are extruded onto the flexible material 12 with a conventional hot melt glue gun, and they are then calendered or flattened via a compression roll to a thickness which determines the desired glue stays 100 stiffness. That is, the stiffness is predominantly a function of glue stays 100 thickness. Glue stays 100 thickness preferably ranges from about 0.3 mm to about 5 mm. After glue stays 100 are applied to an inner layer of the flexible material 12, other layers are combined. Alternatively, if glue stays 100 are to be located on the outer surface 30 or on the body-facing surface 28 of wrap 10, they could be placed there after the wrap layers were combined.

Alternatively, stays 100 may be made of rigid plastic or metal because these material may be applied more easily and are less costly to include. With rigid plastic and metal stays, pockets are typically sewn into wrap 10, and then individual stays are formed and installed.

Body-facing surface 28 of flexible material 12 may optionally comprise foamed polymer strips aligned transverse to longitudinal axis 18 of material 12 for increasing friction between knee wrap 10 and wearer's knee. If present, foamed polymer strips are typically located adjacent second end 16 and interfacial line 54. These strips are generally positioned in a relatively low-motion zone of the knee during bending and straightening thereof. The foamed strips experience relatively little expansion or contraction in a direction transverse to longitudinal axis 18. The increased friction provided by foamed polymer strips serves to reduce slippage or relative movement between knee wrap 10 and the wearer. The foamed polymer strips may also be made visually different (e.g. color) from material 12. This difference can be used by the user as a visual aid in identifying body-facing surface 28. If present, the foam strips are typically about 25 mm wide and about 1.5 mm thick. Alternatively, a high-tack polymer such as ethylene vinyl acetate copolymer (EVA) may be used instead of foamed polymer strips to provide the high friction and/or visual alignment features. The polymer strips, intended for providing friction with the knee to maintain position control, may also serve as stays 100. The polymer strips may be glued, thermally bonded or printed onto body-facing surface 28.

Elastic thermal knee wrap 10 also comprises one or more thermal packs 22. Thermal pack 22 comprises a plurality of individual heat cells 75, preferably embedded within the laminate structure of the thermal pack 22, and applies heat energy to the sides and top of the knee when flexible material 12 is stretched around the user's knee. Heat cells 75 are spaced apart from each other and each heat cell 75 functions independently of the rest of the heat cells 75. Each heat cell 75 preferably comprises a densely packed, particulate exothermic composition 74 which substantially fills the available cell volume within the cell reducing any excess void volume thereby minimizing the ability of the particulate matter to shift within the cell. Alternatively, exothermic composition 74 may be compressed into a hard tablet before being placed in each cell. Because the heat generating material is densely packed or compressed into a tablet, heat cells 75 is not readily flexible. Therefore, the spacing apart of heat cells 75 and the materials selected for base material 70 and cover material 72 between heat cells 75 allows thermal pack 22 to easily conform to the user's knee.

Base material 70 and/or cover material 72 are preferably continuous layers which may be made of any number of suitable materials. Preferably base material 70 and/or cover material 72 comprise materials which are semirigid at a temperature of about 25° C. and which soften, i.e., become substantially less rigid, at a temperature of about 35° C., or greater. That is, the materials preferably have a tensile strength, within the elastic deformation range of the material, of about 0.7 g/mm$^2$ or greater, more preferably about 0.85 g/mm$^2$ or greater, most preferably about 1 g/mm$^2$ or greater, at about 25° C. and a tensile strength substantially less at about 35° C. or greater. "Substantially less", as used herein, means that the tensile strength of the material at about 35° C., or greater, is statistically significantly less than the tensile strength at about 25° C., at an appropriate statistical confidence (i.e., 95%) and power of 90% or greater. Therefore, when heat cells 75, which are fixed within or to the unified structure of thermal pack 22, are active, that is at a heat cell temperature of from about 35° C. to about 60° C., preferably from about 35° C. to about 50° C., more preferably from about 35° C. to about 45° C., and most preferably from about 35° C. to about 40° C., the narrow portion of the continuous layer or layers of material immediately surrounding each heat cell softens and acts as a hinge between the heat cells and between any remaining, cooler, more rigid portions of the continuous layer or layers, bending preferentially more than either the heat cells or any more rigid portion. This results in thermal packs 22 which possess sufficient rigidity to maintain structural support of the heat cells and to prevent unacceptable stretching of structures of the continuous layer or layers during processing or use, while still maintaining good overall drape characteristics when heated.

When thermal packs 22 of the present invention are incorporated into knee wrap 10, knee wrap 10 easily adapts to the contours of the user's knee, provides consistent, convenient, and comfortable heat application, and an excellent conformity with user's knee, while retaining sufficient rigidity to prevent wrap 10 from folding or bunching during use and deter easy access to heat cell contents.

Typically, the tensile strength is measured using a simple tensile test on an electronic tensile test apparatus, such as a universal constant rate elongation tensile testing machine with computer, Instron Engineering Corp., Canton, Mass. Any standard tensile test may be used, for example, material samples are cut into strips having a width of about 2.54 cm (about 1 inch) and a length of from about 7.5 cm to about 10 cm (about 3 to about 4 inches). The ends of the strips are placed into the jaws of the apparatus with enough tension to eliminate any slack, but without loading the load cell. The temperature of the sample is then allowed to stabilize at the desired test temperature. The load cell of the apparatus is set for about 22.7 kg (50 pound) load, the elongation set for 5 mm, and the crosshead speed is set for about 50 cm/min. The apparatus is started and the tensile strength data is collected by the computer. The sample is then removed from the apparatus.

The tensile strength may be calculated as the slope of the tensile load vs. the extension during elastic deformation of the materials using the equation:

$$m=(L/E)$$

Where m=the slope in $g/mm^2$ during elastic deformation;

L=the load at extension in g/mm; and

E=the extension in mm.

The continuous layers of base material 70 and/or cover material 72 also preferably comprise at least two-dimensional drape at about 25° C., i.e., a single fold or crease occurs in the material along a single axis, and preferably three-dimensional drape at about 35° C. or greater, i.e., two or more folds or creases occur along multiple axes. Drape may be determined by placing and centering a square sample, for example about 30 cm by about 30 cm (about 12 inches by about 12 inches), of material on the end of a cylindrical shaft with a pointed end, allowing the material to drape due to gravitational forces, and the number of fold lines counted. Materials that exhibit one-dimensional drape, i.e., have no folds or creases in any direction, are determined to be rigid, while materials that exhibit at least two-dimensional drape, i.e., have at least one fold or crease line forming along at least one axis, are determined to be semirigid.

Different materials may be capable of satisfying the specified requirement for base material 70 and/or cover material 72, provided that the thickness is adjusted accordingly. Such materials include, but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof. These materials may be used alone, preferably extruded, more preferably coextruded, most preferably coextruded with a low melt temperature polymer including, but not limited to, ethylene vinyl acetate copolymer, low density polyethylene, and mixtures thereof.

Base material 70 and/or cover material 72 preferably comprise polypropylene, more preferably a coextruded material comprising polypropylene, most preferably a coextruded material wherein a first side comprises polypropylene, preferably from about 10% to about 90%, more preferably from about 40% to about 60% of the total thickness of the material, and a second side comprises a tie-layer of a low melt temperature copolymer, preferably EVA. Base material 70 and/or cover material 72 preferably have a basis weight thickness of less than about 50 μm, more preferably less than about 40 μm, most preferably less than about 30 μm.

Base material 70 and/or cover material 72 preferably comprise a coextruded material, having a first side of polypropylene and a second side of EVA, and having a combined thickness of from about 20 μm to about 30 μm, preferably about 25 μm (1 mil), wherein the polypropylene comprises about 50% and the EVA tie-layer comprises about 50%, of the total thickness of base material 70 or cover material 72. A particularly suitable material is available as P18-3161 from Clopay Plastics Products, Cincinnati, Ohio. The P18-3161 which is preferred for cover material 72 has been subjected to a post process aperturing with hot needles to render it permeable to oxygen.

When coextruded materials of the type just described are used for base material 70 and cover material 72, the EVA sides are preferably oriented toward each other to facilitate thermal bonding of cover material 72 to base material 70.

Good overall drape characteristics and/or excellent conformity with user's knee, and/or increased structural support to the thermal pack 22, may also be achieved by selectively placing the heat cells 75 into positions fixed within or to the unified structure of the thermal pack 22 relative to each other which are sufficiently close so as to block some or all possible axes across the material of the continuous layer and/or layers 70 and/or 72, which otherwise would have passed uninterrupted between the heat cells 75, through the thermal pack 22, or select regions thereof, to minimize or eliminate undesirable, uninterrupted fold lines. That is, placement of the heat cells 75 into positions relative to each other which are sufficiently close so that the number of axes which pass uninterrupted, between the heat cells 75, is selectively controlled, such that the continuous base layer 70 and cover layer 72 of thermal pack 22, or select regions thereof, preferably folds along a multiplicity of short interconnected fold lines oriented in a number of different directions relative to each other. Folding along a multiplicity of interconnected fold lines results in thermal packs 22 which have good overall drape characteristics, readily conform with user's knee, and/or have increased structural support of the heat cell matrix.

Because heat cells 75 are not readily flexible, the spacing between heat cells 75 provides the preferred benefits and may be determined, when selectively placing heat cells 75 within or fixed to the unified structure of thermal packs 22, wherein at least one heat cell of four adjacent heat cells, whose centers form a quadrilateral pattern, blocks one or more axes that could otherwise form at least one fold line tangential to the edges of one or more pairings of the remaining three heat cells in the quadrilateral pattern. Preferably, the spacing between at least one heat cell of the four adjacent heat cells and each of the heat cells of the one or more pairings of the remaining heat cells in the quadrilateral pattern may be calculated using the equation:

$$s \leq (W_q/2)*0.75$$

Where s=the closest distance between the heat cells; and $W_q$=the measurement of the smallest diameter of the smallest diameter heat cell within the quadrilateral pattern.

Alternatively, the spacing between heat cells 75 may be determined wherein, at least one heat cell of three adjacent heat cells, whose centers form a triangular pattern, blocks one or more axes that could otherwise form at least one fold line tangential to the edges of the remaining pair of heat cells in the triangular pattern formed by the three heat cells. Most preferably, the spacing between at least one heat cell of the three adjacent heat cells and each heat cell of the remaining pair of heat cells in the triangular pattern may be calculated using the equation:

$$s \leq (W_t/2)*0.3$$

Where s=the closest distance between the heat cells; and $W_r$=the measurement of the smallest diameter of the smallest diameter heat cell within the triangular pattern.

Different materials may be capable of satisfying the above specified requirements. Such materials may include, but are not limited to, those materials mentioned above.

A most preferred embodiment of the disposable thermal packs 22 of the present invention comprises at least one continuous layer of semirigid material having the thermophysical properties described above, and the heat cells 75 fixed within or to the unified structure of thermal pack 22 in positions relative to each other which are sufficiently close so as to block some or all possible axes across the material of the continuous material(s) 70 and/or 72, which otherwise would have passed uninterrupted between heat cells 75, through thermal packs 22, or select regions thereof, to minimize or eliminate undesirable, uninterrupted fold lines, as described above.

Exothermic composition 74 may comprise any composition capable of providing heat. However, exothermic composition 74 preferably comprises a particulate mix of chemical compounds that undergo an oxidation reaction during use. Alternatively, exothermic composition 74 may also be formed into agglomerated granules, direct compacted into compaction articles such as granules, pellets, tablets, and/or slugs, and mixtures thereof. The mix of compounds typically comprises iron powder, carbon, a metal salt(s), and water. Mixtures of this type, which react when exposed to oxygen, provide heat for several hours.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air. Typically, the iron powder comprises from about 30% to about 80% by weight, preferably from about 50% to about 70% by weight, of the particulate exothermic composition.

Active carbon prepared from coconut shell, wood, charcoal, coal, bone coal, etc. are useful, but those prepared from other raw materials such as animal products, natural gas, fats, oils and resins are also useful in the particulate exothermic composition of the present invention. There is no limitation to the kinds of active carbon used, however, the preferred active carbon has superior water holding capabilities and the different carbons may be blended to reduce cost. Therefore, mixtures of the above carbons are useful in the present invention as well. Typically, activated carbon, non-activated carbon, and mixtures thereof, comprises from about 3% to about 25%, preferably from about 8% to about 20%, most preferably from about 9% to about 15% by weight, of the particulate exothermic composition.

The metal salts useful in the particulate exothermic composition include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof. Typically, the metal salt(s) comprises from about 0.5% to about 10% by weight, preferably from about 1.0% to about 5% by weight, of the particulate exothermic composition.

The water used in the particulate exothermic composition may be from any appropriate source. There is no particular limitation to its purity, kind, etc. Typically, water comprises from about 1% to about 40% by weight, preferably from about 10% to about 30% by weight, of the particulate exothermic composition.

Additional water-holding materials may also be added as appropriate. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts, and other porous materials having a large capillary function and hydrophilic property can be used. Typically, the additional water-holding materials comprise from about 0.1% to about 30% by weight, preferably from about 0.5% to about 20% by weight, most preferably from about 1% to about 10% by weight, of the particulate exothermic composition.

Other additional components include agglomeration aids such as gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup; dry binders such as maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate; oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and α-starch, and surfactants such as those included within the anionic, cationic, nonionic, zwitterionic, and amphoteric types. The preferred surfactant, if used however, is nonionic. Still other additional components which may be added to the particulate exothermic compositions of the present invention, as appropriate, include extending agents such as metasilicates, zirconium, and ceramics.

Preferably at least 50%, more preferably 70%, even more preferably 80% and most preferably 90% of all of the particles by weight of the particulate exothermic composition of the present invention have a mean particle size of less than 200 μm, preferably less than 150 μm.

The above-mentioned components of the composition are blended using conventional blending techniques. Suitable methods of blending these components are described in detail in U.S. Pat. No. 4,649,895 to Yasuki et al., issued Mar. 17, 1987 which is incorporated by reference herein in its entirety.

Alternatively to the above described particulate exothermic composition, the exothermic composition may be formed into agglomerated granules, direct compacted into compaction articles such as granules, pellets, tablets, and/or slugs, and mixtures thereof.

The exothermic composition of these agglomerated granules and/or compaction articles comprises iron powder, dry powdered carbonaceous material, an agglomeration aid, and a dry binder. Additionally, a metal salt, is added to the dry mix or subsequently as an aqueous/brine solution. Typically, the iron powder comprises from about 30% to about 80%, preferably from about 40% to about 70%, most preferably from about 50% to about 65% by weight; activated carbon, non-activated carbon, and mixtures thereof, comprises from about 3% to about 20%, preferably from about 5% to about 15%, most preferably from about 6% to about 12% by weight; the metal salt(s) comprises from about 0.5% to about 10%, preferably from about 1% to about 8%, most preferably from about 2% to about 6% by weight; the agglomeration aids comprise from about 0% to about 9%, preferably from about 0.5% to about 8%, more preferably from about 0.6% to about 6%, most preferably from about 0.7% to about 3% by weight; and the dry binder comprises from about 0% to about 35%, preferably from about 4% to about 30%, more preferably from about 7% to about 20%, most preferably from about 9% to about 15% by weight, of the agglomerated pre-compaction compositions of the present invention.

Heat cells comprising agglomerated granules are typically made using conventional blending techniques and agglomerated into granules.

Heat cells comprising compaction articles are preferably made by direct compaction of the dry ingredients into articles such as hard granules, pellets, tablets, and/or slugs. Suitable methods of making tablets and/or slugs are described in detail in Chapter 89, "Oral Solid Dosage Forms", *Remington's Pharmaceutical Sciences,* 18th Edition, (1990), pp. 1634–1656, Alfonso R. Gennaro, ed., incorporated herein by reference in its entirety. Any conventional tableting machine and compression pressures, up to the maximum provided by the machine can be used.

The tablets/slugs can have any geometric shape consistent with the shape of the heat cell, e.g., disk, triangle, square, cube, rectangle, cylinder, ellipsoid and the like, all or none of which may contain a hole through the middle or other reservoir. The preferred shape of the tablet/slug comprises a disk shaped geometry, having a concaved (whisper) configuration to the top and/or bottom of the tablet. The more preferred shape of the tablet/slug, however, comprises a disk shaped geometry, having a hole perpendicular to, and through the middle of the top and bottom of the tablet.

The size of the compacted disk is limited only by the size of the punches and die available and/or used in the tableting machine, as well as the size of the heat cell pocket. However, the disk typically has a diameter of from about 0.2 cm to about 10 cm, preferably from about 0.5 cm to about 8 cm, more preferably from about 1 cm to about 5 cm, and most preferably from about 1.5 cm to about 3 cm and a height of from about 0.08 cm to about 1 cm, preferably from about 0.15 cm to about 0.86 cm, more preferably from about 0.2 cm to about 0.6 cm, and most preferably from about 0.2 cm to about 0.5 cm. Alternatively, the compacted disk having a geometric shape other than a disk shape may have a width at its widest point of from about 0.15 cm to about 20 cm, preferably from about 0.3 cm to about 10 cm, more preferably from about 0.5 cm to about 5 cm, most preferably from about 1 cm to about 3 cm, a height at its highest point of from about 0.08 cm to about 1 cm, preferably from about 0.15 cm to about 0.8 cm, more preferably from about 0.2 cm to about 0.6 cm, and most preferably from about 0.2 cm to about 0.5 cm, and a length at its longest point of from about 1.5 cm to about 20 cm, preferably from about 1 cm to about 15 cm, more preferably from about 1 cm to about 10 cm, most preferably from about 3 cm to about 5 cm. The hole or reservoir should be large enough to substantially hold the prescribed amount of water and/or the water-carrying material. Typically, the hole has a diameter of from about 0.1 cm to about 1 cm, preferably from about 0.2 cm to about 0.8 cm, and more preferably from about 0.2 cm to about 0.5 cm.

The compaction articles of the present invention are compressed to the hardest possible mechanical strength to withstand the shocks of handling in their manufacture, packing, shipping, and dispensing. The compaction articles are typically compressed to a density of greater than about 1 g/cm$^3$, preferably from about 1 g/cm$^3$ to about 3 g/cm$^3$, more preferably from about 1.5 g/cm$^3$ to about 3 g/cm$^3$, and most preferably from about 2 g/cm$^3$ to about 3 g/cm$^3$.

Heat cells 75 comprising the above described components are typically formed by adding a fixed amount of a particulate exothermic composition or compaction article(s) 74 to a pocket or pockets made in a first continuous layer, i.e., cell base material 70. A second continuous layer, i.e., cover material 72, is placed over the first continuous layer, sandwiching the particulate exothermic composition or compaction article(s) between the two continuous layers which are then bonded together, preferably using a low heat, forming a unified, laminate structure. Preferably, each heat cell has a similar volume of heat generating material and has similar oxygen permeability means. However, the volume of the heat generating material, shape of the heat cell, and oxygen permeability may be different from heat cell to heat cell as long as the resulting cell temperatures generated are within accepted therapeutic and safety ranges for their intended use.

The heat cells 75 of thermal pack 22 can have any geometric shape, e.g., disk, triangle, pyramid, cone, sphere, square, cube, rectangle, rectangular parallelepiped, cylinder, ellipsoid and the like. The preferred shape of the heat cells 75 comprises a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm. The heat cells 75 have a height of from greater than about 0.2 cm to about 1 cm, preferably from greater than about 0.2 cm to about 0.9 cm, more preferably from greater than about 0.2 cm to about 0.8 cm, and most preferably from greater than about 0.3 cm to about 0.7 cm. Alternatively, the heat cells having geometric shapes other than a disk shape, preferably an ellipsoid (i.e., oval), may have a width at its widest point of from about 0.15 cm to about 20 cm, preferably from about 0.3 cm to about 10 cm, more preferably from about 0.5 cm to about 5 cm, most preferably from about 1 cm to about 3 cm, a height at its highest point of from greater than about 0.2 cm to about 5 cm, preferably from greater than about 0.2 cm to about 1 cm, more preferably from greater than about 0.2 cm to about 0.8 cm, and most preferably from about 0.3 cm to about 0.7 cm and a length at its longest point of from about 0.5 cm to about 20 cm, preferably from about 1 cm to about 15 cm, more preferably from about 1 cm to about 10 cm, most preferably from about 3 cm to about 5 cm.

Heat cells 75 of thermal pack 22 can have any geometric shape, e.g., disk, triangle, pyramid, cone, sphere, square, cube, rectangle, rectangular parallelepiped, cylinder, ellipsoid and the like. The preferred shape of heat cell 75 comprises a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm. Heat cell 75 has a height of from about 0.08 cm to about 1 cm, preferably from about 0.15 cm to about 0.9 cm, more preferably greater than from about 0.2 cm to about 0.8 cm, and most preferably about 0.4 cm.

The ratio of fill volume to cell volume of heat cell 75 is from about 0.7 to about 1.0, preferably from about 0.75 to about 1.0, more preferably from about 0.8 to about 1.0, even more preferably from about 0.85 to about 1.0, and most preferably from about 0.9 to about 1.0.

Oxygen permeability can be provided by selecting materials for the base material 70 and/or cover material 72 that have the specifically desired permeability properties. The desired permeability properties may be provided by microporous films or by films which have pores or holes formed therein. The formation of these holes/pores may be via extrusion cast/vacuum formation or by hot needle aperturing. Oxygen permeability can also be provided in the present invention by perforating at least one of the base material 70 and cover material 72 with aeration holes using, for example, an array of pins having tapered points and diameters of from about 0.2 mm to about 2 mm, preferably from about 0.4 mm to about 0.9 mm. The array of pins is patterned such that the base material 70 and/or cover material 72 are perforated by from about 10 to about 30 pins per square centimeter. Alternatively, after the base material 70 and cover material 72 have been bonded together, enclosing the exothermic composition 74 in the pocket 76 between them, at least one side of heat cell 75 may be perforated with aeration holes using, for example, at least one pin, preferably an array of from about 20 to about 60 pins having tapered points and diameters of from about 0.2 mm to about 2 mm, preferably from about 0.4 mm to about 0.9 mm. The pins are pressed through one side of the base material 70 and/or cover material 72 to a depth of from about 2% to about 100%, preferably from about 20% to about 100%, and more preferably from about 50% to about 100% into the exothermic composition 74. This hole configuration provides an oxygen diffusion into heat cell 75 during oxidation of the particulate exothermic composition 74 of from about 0.01 cc $O_2$/min./5 cm$^2$ to about 15.0 cc $O_2$/min./5 cm$^2$ (at 21° C., 1 ATM), preferably from about 0.9 cc $O_2$/min./5 cm$^2$ to about 3 cc $O_2$/min./5 cm$^2$ (at 21° C., 1 ATM).

The velocity, duration, and temperature of the thermogenic oxidation reaction of the exothermic composition 74 can be controlled as desired by changing the area of contact with air, more specifically, by changing the oxygen diffusion/permeability.

Elastic thermal knee wrap 10 may optionally comprise a layer of material located preferably on body-facing surface 28 of material 12. The layer of material is generally coextensive material 12 from second end 16 to interfacial centerline 54. The layer of material has elasticity in a direction transverse to longitudinal axis 18 of material 12. Preferably, the layer of material has an elastic recovery force which is as low as possible to minimize forces transverse to longitudinal axis 18 so that material 12 will not be bunched or pulled off the upper leg when the user's knee is flexed. The layer of material is typically attached to body-facing surface 28 of material 12 along the perimeter of the layer of material using an adhesive. The layer of material provides coverage of the knee when the user's knee is bent and material 12 expands separating slit(s) 48.

The layer of material may be any number of suitable materials. One material that has been used successfully is a trilaminate made from two layers of carded, thermally bonded polypropylene (TBPP) nonwoven and an elastic scrim therebetween. The nonwoven used is a 27 gsy nonwoven available from Fibertech, Landisville, N.J., as white TBPP, brand #67050. The scrim used is from Conwed Plastics, Minneapolis, Minn., as TN4631 plastic netting. All three layers are assembled using a pressure sensitive hot melt glue available from Findley Adhesives, Wawautosa, Wis., as 2031 adhesive. The glue is applied via a spiral application method by Waytek, Springboro, Ohio, at a level of 0.002 to 0.006 grams per square inch. The trilaminate is assembled with the elastic scrim under zero strain. The assembled trilaminate is then passed between a pair of matched ring rolls with an engagement of about 2 mm to break the nonwoven on a fine scale and allow the elastic scrim to stretch.

The layer of material is attached along its perimeter to material 12 by a double sided adhesive tape available from 3M, St. Paul, Minn., as 1524 adhesive tape. A variety of different methods could be used to attach the layer of material to material 12 including, but not limited to, hot melt adhesive, pressure sensitive adhesives, ultrasonic bonding, pressure bonding, etc. Adhesives, if used, can be applied via hot melt beads, foam, spiral hot melt, melt blown, spray, immersion, transfer, etc.

Alternatively the layer of material may have elasticity in a direction parallel to longitudinal axis 18 in addition to elasticity in a direction transverse to longitudinal axis 18. The addition of elasticity in a direction parallel to longitudinal axis 18 in the layer of material provides material 12 with the ability to stretch and recover during the flexing of the knee which minimizes gapping or wrinkling of wrap 10 during wear.

The elastic thermal knee wrap may further optionally comprise a stripe of high-tack poymer fixably attached to the body-facing surface 28 of the knee wrap 10, transverse to the longitudinal axis 18 of the piece of flexible material 12, for increasing friction between the knee wrap 10 and a user's leg in order to reduce slippage of the wrap 10 during use.

The disposable thermal knee wraps of the present invention may optionally incorporate a component, such as a separate substrate layer or incorporated into at least one of the continuous layers, comprising active aromatic compounds, non-active aromatic compounds, pharmaceutical actives or other therapeutic agents, and mixtures thereof, to be delivered through the skin. Such active aromatic compounds include, but are not limited to, menthol, camphor, and eucalyptus. Such non-active aromatic compounds include, but are not limited to, benzaldehyde, citral, decanal, and aldehyde. Such pharmaceutical actives/therapeutic agents include, but are not limited to antibiotics, vitamins, antiviral agents, analgesics, anti-inflammatory agents, antipruritics, antipyretics, anesthetic agents, antifungals, antimicrobials, and mixtures thereof. The disposable thermal knee wraps may also comprise a separate substrate layer, or incorporated into at least one of the continuous layers, a self-adhesive component and/or a sweat-absorbing component.

The finished disposable thermal knee wraps are typically packaged in a secondary package. An air-impermeable package may be used to prevent an oxidation reaction from occurring until desired as described in U.S. Pat. No. 4,649,895, incorporated herein by reference in its entirety. Alternatively, other means may also be used to prevent an oxidation reaction from occurring before desired, such as air impermeable removable adhesive strips placed over the aeration holes in the heat cells such that, when the strips are removed, air is allowed to enter the heat cells, thus activating the oxidation reaction of the iron powder.

The present invention further comprises a method for treating acute, recurrent, and/or chronic knee pain, including muscular, skeletal, and/or referred knee pain, of a person suffering such pain by topically applying heat to the knee of a person suffering such pain. The method comprises maintaining a skin temperature to the knee of a person suffering such pain of from about 32° C. to about 50° C., preferably from about 32° C. to about 45° C., more preferably from about 32° C. to about 42° C., most preferably from about 32° C. to about 39° C., still most preferably from about 32° C. to about 37° C., preferably by applying the above described knee wraps to the knee of a person suffering such pain, for from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment, such that the desired therapeutic benefits are achieved, without any adverse events, such as skin burns which may be incurred by using a high temperature for a long period of time.

Preferably the method comprises maintaining a sustained skin temperature to the knee of a person having acute, recurrent, and/or chronic knee pain, including muscular, skeletal, and/or referred knee pain, of from about 32° C. to about 43° C., preferably from about 32° C. to about 42° C., more preferably from about 32° C. to about 41° C., most preferably from about 32° C. to about 39° C., still most preferably from about 32° C. to about 37° C., for a time period of greater than about 1 hour, preferably greater than about 4 hours, more preferably greater than about 8 hours, even more preferably greater than about 16 hours, most preferably about 24 hours, to substantially relieve acute, recurrent, and/or chronic knee pain, including skeletal, muscular, and/or referred knee pain, of a person having such pain and to substantially prolong relief, for at least about two hours, preferably for at least about 8 hours, more preferably for at least about sixteen hours, most preferably for at least about one day, still most preferably for at least about three days, from such pain, even after the heat source is removed from the knee of the user.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable elastic thermal knee wrap comprising:
   a) at least one piece of flexible material having a body portion, a first end, a second end, and one or more elastic portions therebetween said first end and said second end, wherein said elastic portion is stretchable along a longitudinal axis of said piece of flexible material, said piece of flexible material having a length adapted to encircle a user's knee such that said first and second ends overlap;
   b) one or more thermal packs fixedly attached to said piece of flexible material, said thermal pack having a unified structure comprising at least one continuous layer of a semirigid material having a tensile strength of about 0.7 g/mm$^2$, or greater, and at least two-dimensional drape at a temperature of about 25° C., and wherein said material has a tensile strength, at a temperature of about 35° C. or greater, substantially less than said tensile strength of said material at about 25° C., and having a plurality of individual heat cells spaced apart and fixed within or to said unified structure of said thermal pack; and
   c) a fastening means fixedly attached near or to at least one of said first and second ends of said piece of flexible material in order to hold said thermal knee wrap around said user's knee;

wherein said body portion further comprises an aperture intended to be aligned with the user's patella to establish a convenient locating portion for wrapping said knee wrap around the user's knee and wherein said body portion still further comprises at least one slit extending substantially along said longitudinal axis from said aperture for enabling said piece of flexible material to stretch transverse to said longitudinal axis at said aperture in order to accommodate bending of the user's knee.

2. A disposable thermal knee wrap according to claim 1 wherein said at least one continuous layer comprises a tensile strength of about 0.85 g/mm$^2$, or greater, and at least two-dimensional drape at a temperature of about 25° C.

3. A disposable thermal knee wrap according to claim 1 wherein said at least one continuous layer comprises a tensile strength of about 1 g/mm$^2$, or greater, and at least two-dimensional drape at a temperature of about 25° C.

4. A disposable thermal knee wrap according to claim 1 wherein said at least one continuous layer comprises a material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

5. A disposable thermal knee wrap according to claim 4 wherein said at least one continuous layer comprises an extruded material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer.

6. A disposable thermal knee wrap according to claim 5 wherein said at least one continuous layer comprises a coextruded material having a first side selected from the group consisting of polyethylene, polypropylene, nylon, polyester, polyvinyl chloride, polyvinylidene chloride, polyurethane, and polystyrene, and a second side selected from the group consisting of saponified ethylene-vinyl acetate copolymer and ethylene-vinyl acetate copolymer.

7. A disposable thermal knee wrap according to claim 6 wherein said at least one continuous layer comprises a coextruded material having a first side of polypropylene and a second side of ethylene-vinyl acetate copolymer.

8. A disposable thermal knee wrap according to claim 7 wherein said at least one continuous layer comprises a coextruded material having a first side of polypropylene and a second side of ethylene vinyl acetate copolymer, wherein said polypropylene comprises from about 10% to about 90% of the total thickness of said material.

9. A disposable thermal knee wrap according to claim 7 wherein said at least one continuous layer comprises a coextruded material having a first side of polypropylene and a second side of ethylene vinyl acetate copolymer, wherein said polypropylene comprises from about 40% to about 60% of the total thickness of said material.

10. A disposable elastic thermal knee wrap according to claim 4 wherein said flexible material further comprises one or more strap portions.

11. A disposable elastic thermal knee wrap according to claim 10 wherein said strap portions are elastic.

12. A disposable elastic thermal knee wrap according to claim 4 wherein said flexible material further comprises one or more stays to resiliently stiffen said flexible material and thereby minimize bunching of said flexible material when said user's knee is repeatedly bent.

13. A disposable elastic thermal knee wrap according to claim 1 wherein said fastening system is reclosable.

14. A disposable elastic thermal knee wrap according to claim 13 wherein said reclosable fastening system comprises a hook and loop fastening system.

15. A disposable elastic thermal knee wrap according to claim 14 wherein said reclosable fastening system comprises a two-part hook and loop fastening system.

16. A disposable thermal knee wrap according to claim 1 wherein said heat cells comprise an exothermic composition comprising:
   a.) from about 30% to about 80% by weight, iron powder;
   b.) from about 3% to about 25% by weight, carbonaceous material selected from the group consisting of activated carbon, non-activated carbon, and mixtures thereof;
   c.) from about 0.5% to about 10% by weight, metal salt; and
   d.) from about 1% to about 40% by weight, water.

17. A disposable thermal knee wrap according to claim 16 wherein said heat cells comprise a shape selected from the group consisting of a disk, triangle, pyramid, cone, sphere, square, cube, rectangle, rectangular parallelepiped, cylinder, and ellipsoid, said disk having a diameter of from about 1 cm to about 5 cm and a height of from greater than about 0.2 cm to about 1 cm, and said triangle, pyramid, cone, sphere, square, cube, rectangle, rectangular parallelepiped, cylinder, and ellipsoid having a width at its widest point of from about 0.5 cm to about 5 cm and a height at its highest point of from greater than about 0.2 cm to about 1 cm and a length at its longest point of from about 1.5 cm to about 10 cm.

18. A disposable thermal knee wrap according to claim 16 further comprising additional components selected from the group consisting of active aromatic compounds, non-active aromatic compounds, pharmaceutical actives, and mixtures thereof.

19. A disposable thermal knee wrap according to claim 17 wherein said heat cells, when filled with said exothermic composition, have a fill volume to cell volume ratio of from about 0.7 to about 1.0.

20. A disposable thermal knee wrap according to claim 19 wherein said exothermic composition further comprises from about 0.1% to about 30% by weight, of additional water-holding material.

21. A disposable thermal knee wrap according to claim 1 wherein said heat cells comprise an exothermic composition comprising:
   a.) from about 30% to about 80% by weight, of iron powder;
   b.) from about 3% to about 20% by weight, carbonaceous material selected from the group consisting of activated carbon, non-activated carbon, and mixtures thereof;
   c.) from about 0% to about 9% by weight, of an agglomeration aid selected from the group consisting of gelatin, natural gums, cellulose derivatives, cellulose ethers and their derivatives, starch, modified starches, polyvinyl alcohols, polyvinylpyrrolidone, sodium alginates, polyols, glycols, sucrose syrup, corn syrup, maltitol syrup, sorbitol syrup other polysaccharides and their derivatives, polyacrylamides, polyvinyloxoazolidone, and mixtures thereof; and
   d.) from about 0% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof;
wherein from about 0.5% to about 10% by weight, of a metal salt selected from the group consisting of alkali metal salts, alkaline earth metal salts, transitional metal salts, and mixtures thereof is added to said composition, as part of the dry mix or after compaction, in an aqueous solution as brine, and wherein said exothermic composition comprises a physical form selected from the group consisting of dry agglomerated granules, direct compaction articles, and mixtures thereof, wherein said direct compaction articles are selected from the group consisting of granules, pellets, tablets, slugs, and mixtures thereof, and wherein said tables and slugs comprise a geometric shape selected from the group consisting of disk, triangle, square, cube, rectangle, cylinder, and ellipsoid, said disk having a diameter of from about 1 cm to about 5 cm and a height of from about 0.08 cm to about 1 cm and said triangle, square, cube, rectangle, cylinder, and ellipsoid having a width at its widest point of from about 0.5 cm to about 5 cm and a height at its highest point of from about 0.08 cm to about 1 cm and a length at its longest point of from about 1 cm to about 10 cm.

22. A disposable thermal knee wrap according to claim 21 wherein said exothermic composition further comprises from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

23. A disposable thermal knee wrap according to claim 21 wherein said exothermic composition comprises from about 4% to about 30% by weight, of said dry binder of microcrystalline cellulose.

24. A disposable thermal knee wrap according to claim 23 wherein said exothermic composition comprises from about 0.5% to about 8% by weight, of said agglomeration aid selected from the group consisting of corn syrup, maltitol syrup, crystallizing sorbitol syrup, amorphous sorbitol syrup, and mixtures thereof.

25. A disposable thermal knee wrap according to claim 23 wherein said direct compaction articles comprise a density of greater than about 1 g/cm$^3$.

26. A disposable thermal knee wrap according to claim 1 wherein said one or more thermal packs comprise a unified structure having at least one continuous layer of material and a plurality of individual heat cells placed into positions fixed within or to said unified structure of said thermal pack which are sufficiently close and relative to each other, so as to block some or all possible axes across said at least one continuous layer, which otherwise would have passed uninterrupted between said heat cells, through said thermal pack, or select regions thereof, to minimize or eliminate uninterrupted fold lines across said continuous layer.

27. A disposable thermal knee wrap according to claim 26 wherein at least one of said heat cells of four adjacent said heat cells, whose centers form a quadrilateral pattern, blocks one or more of said axes that could otherwise form at least one fold line tangential to the edges of one or more pairings of the remaining said heat cells in the quadrilateral pattern.

28. A disposable thermal knee wrap according to claim 27 wherein the spacing between said at least one of said heat cells and each of said heat cells of said one or more pairings of said remaining heat cells in said quadrilateral pattern is the same or less than the spacing obtained by dividing the measurement of the smallest diameter of the smallest diameter heat cell of said heat cells within said quadrilateral pattern by 2 and multiplying the result by 0.75.

29. A disposable thermal knee wrap according to claim 26 wherein at least one of said heat cells of three adjacent said heat cells, whose centers form a triangular pattern, blocks one or more of said axes that could otherwise form at least one fold line tangential to the edges of the remaining pair of said heat cells in the triangular pattern formed by said three heat cells.

30. A disposable thermal knee wrap according to claim 29 wherein the spacing between said at least one of said heat cells and each of said heat cells of said remaining pair of said heat cells in said triangular pattern is the same or less than the spacing obtained by dividing the measurement of the smallest diameter of the smallest diameter heat cell of said heat cells within said triangular pattern by 2 and multiplying the result by 0.3.

* * * * *